United States Patent [19]

Shanbrom

[11] 4,069,216

[45] Jan. 17, 1978

[54] SIMPLIFIED METHODS FOR PREPARATION OF VERY HIGH PURITY FACTOR VIII CONCENTRATE

[75] Inventor: Edward Shanbrom, Santa Ana, Calif.

[73] Assignee: Edward Shanbrom, Inc., Santa Ana, Calif.

[21] Appl. No.: 653,973

[22] Filed: Jan. 30, 1976

Related U.S. Application Data

[63] Continuation-in-part of Ser. No. 586,948, June 16, 1975.

[51] Int. Cl.$^2$ ................................................. A23J 1/06
[52] U.S. Cl. .................................. 260/112 B; 424/101
[58] Field of Search ..................... 260/112 B; 424/101

[56] References Cited

U.S. PATENT DOCUMENTS

| 3,631,018 | 12/1971 | Shanbrom | 260/112 B |
| 3,652,530 | 3/1972 | Johnson | 260/112 B |
| 3,682,881 | 8/1972 | Fekete | 260/112 B |
| 3,803,115 | 4/1974 | Fekete | 260/112 B |
| 3,839,314 | 10/1974 | Fekete | 260/112 B |
| 3,973,002 | 8/1976 | Hagan | 260/112 B |

OTHER PUBLICATIONS

J. Newman et al., British Journal of Haematology, vol. 21, No. 1, July 1971, pp. 1-20.

Primary Examiner—Paul R. Michl
Attorney, Agent, or Firm—Knobbe, Martens, Olson, Hubbard & Bear

[57] ABSTRACT

A method for concentrating and purifying Factor VIII by selective cold precipitation with polyols is disclosed.

8 Claims, No Drawings

SIMPLIFIED METHODS FOR PREPARATION OF VERY HIGH PURITY FACTOR VIII CONCENTRATE

Related Patent Applications

This is a continuation-in-part of Application Ser. No. 586,948, filed June 16, 1975.

Several different methods have been described for the production of antihemophilic factor (AHF or Factor VIII) for therapeutic use, e.g., selective precipitation, batch absorption and elution, extraction in low ionic media and chromatography. Chemicals most frequently used for precipitation include alcohol, tannic acid, ammonium sulfate, glycine and polyethylene glycol. While purification of Factor VIII entails the elimination of a variety of other plasma proteins, fibrinogen is by far the most important and troublesome of these proteins, particularly when denatured by such processes as alcohol precipitation, freezing and thawing. This denatured fibrinogen impairs filtration of AHF, causes appreciable losses of AHF during purification steps and decreases the solubility of the lyophilized product in reconstituting fluid. Thus, any satisfactory method of purifying AHF requires removal of appreciable quantities of fibrinogen. The selective precipitation techniques described above are designed for this purpose but all have the disadvantages of further denaturing fibrinogen and AHF, or producing undesirable losses of AHF.

Methods utilizing simple cold precipitation without chemicals (cryoprecipitation) are limited to small scale production usually in blood banks, and result in high fibrinogen blood levels when used therapeutically, a feature considered undesirable by some experts in the field.

Procedures which involve the extraction of Factor VIII from cryoprecipitation in low ionic strength buffers, while decreasing the fibrinogen content of the final product somewhat, still have an undesirably high protein content, require special equipment and procedures for centrifugation and are limited in the total amount of AHF which may be extracted from the cryoprecipitate without impairing purification.

Other problems commonly associated with large-scale manufacture of AHF are the contimination of the final product by pyrogenic substances, isohemagglutinens and viruses which cause hepatitis (hepatitis associated antigen, HAA). With some chemical precipitants, these undesirable contaminants may actually be enhanced. Polyethylene glycol is now commonly used in the production of high purity Factor VIII concentrates but these techniques utilize concentrations of the polymer so high that further steps of washing and reprecipitation are required to eliminate excessive amounts of polyethylene glycol from the final product (1, 2, 3, 4). Such processes then lead to additional undesirable losses of AHF (1, 2, 3, 4, 5).

The method herein described virtually eliminates the aforementioned problems, lacks the disadvantages associated with previously described chemical precipitation techniques and relies on the simple procedure of selective cold precipitation of fibrinogen, its denatured and degraded products, and selective concentration of Factor VIII by small amounts of polyol (polyethylene glycol or Pluronic (TM) polyol). Removal of fibrinogen, as discussed hereinafter, includes removal of fibrinogen and its denatured and degraded products.

The selective removal of fibrinogen without associated loss of Factor VIII has not generally been previously accomplished as a practical method for large-scale manufacture of a purified AHF concentrate. In fact, Wickerhauser (1), emphasizes the importance of limiting the time and temperature in extracting AHF. "Somewhat higher yields of AHF were obtained by prolonged Tris extraction at 30° C beyond 60 minutes, but the extract was increasingly contaminated with aggregated fibrinogen which made the final concentrate poorly filterable."

A technique utilizing low temperature selective precipitation of fibrinogen for the large-scale manufacture of high yield, high purity Factor VIII concentrate is the subject of a U.S. patent submission by Shanbrom (7). It was pointed out that the preparation could be further refined and concentrated by utilizing cold polyethylene glycol (PEG) precipitation.

Until recently all methods utilizing PEG in the manufacture of AHF concentrates require an additional step of washing and/or reprecipitation with glycine of alcohol because the polymer is used in high concentrations (10–12%) (1, 2, 3, 7). Vermeer et al (8) recently utilized the idea of cold precipitation with PEG. However, the concentration of PEG used to precipitate fibrinogen was only 2½% resulting in a less purified product. In addition, they did not consider that the protein concentration was important, used mandelate to prevent irreversible precipitation of fibrinogen and, therefore, had a considerably less purified product and a lower yield. Similarly, the method of Shanbrom and Fekete (2) used a relatively low protein concentration during PEG precipitation steps, i.e., 1 volume of precipitate in 10 volumes of dissolving buffer, and this resulted in a very poor yield with limited purity. (These authors, as well as Johnson et al (4, 6) used 10–12% PEG for the final concentration of AHF, thus necessitating an additional step of dissolution and reprecipitation with glycine or cold-ethanol to reduce the PEG content of the final product).

Further evidence that the concentration of protein and cold PEG precipitation are critical and produce a unique product is seen by the fact that the "incomplete" isohemagglutinins (antibodies) have been virtually eliminated, thus avoiding the hazard of hemolytic reactions which may occur when intensive infusions of presently available commercial concentrates are required (9).

A further unique feature of the product resulting from the invention is the high degree of purity (i.e., low protein content) especially in the amount of measurable fibrinogen. This high degree of purity results in a very highly soluble product, so soluble in fact that no undissolved material is left in the vial after reconstitution. This eliminates the need to use a special filter or filter needle to remove the undissolved protein prior to infusion into the patient. Thus, contamination of the Factor VIII concentrate with metal particles is avoided (10).

The method described, or part of it, is also useful in "reworking" pyrogenic lots of Factor VIII concentrates manufactured by any other procedure, thus converting costly pyrogenic, nonutilizable Factor VIII to a valuable, useful therapeutic agent. By either a single-step cold 6% PEG precipitation or by the 2-step method herein described in detail, the pyrogenic material is "washed out" of the reprocessed product.

The unexpected and vastly improved results found and reported here are contrary to the teachings and suggestions of the prior art, and were arrived at in initial stages by the inventor more by coincidence than by design.

This invention is a specific method for the large-scale manufacture of a very high purity Factor VIII concentrate. Among the more unique features of the invention is the selective precipitation of excessive amounts of fibrinogen, its denatured forms and degradation products, the elimination of other undesirable proteins such as isohemagglutinins, and one-step concentration of Factor VIII by cold precipitation with a polyol, without undesirable loss of AHF activity. An additionally outstanding feature is the surprisingly high yield of Factor VIII, approximately 20-40% of the theoretical plasma. In addition, and in spite of the high AHF recovery, the protein content has been strikingly reduced, particularly fibrinogen, compared to other products. This is illustrated in Table I.

A jacketed reaction vessel is used for all dissolution and precipitation steps, with continuous stirring, care being taken to avoid foaming.

The second precipitation step if followed by continuous flow centrifugation at 1°-2° C and the supernatant fluid is discarded. The precipitate is dissolved in glycine-citrate buffer or citrate buffer, the volume depending on the quality of the cryoprecipitate and the number of AHF units assayed in its initial solution. Two methods to calculate this volume are:

1. Dissolve the final precipitate in a volume of buffer equal to 1/100 of the original plasma pool.
2. Dissolve the final precipitate in a volume of buffer equal to 15-25 times the weight of the precipitate.

The solution is then adjusted to a pH of 6.7-6.9 with citric acid, clarified, and then sterilized by passing the liquid through 293mm micropore membrane filters (or

TABLE I [1/]
SOME CHARACTERISTICS OF FACTOR VIII CONCENTRATES [2/]

| | Product | Units Factor VIII/Ml | Total Volume Administered (Ml) | Total Units Factor VIII | Total Fibrinogen (GM) | Total Protein (GM) | Total Sodium (MEQ) | Total Chloride (MEQ) | Total Cost (Dollars) | Source |
|---|---|---|---|---|---|---|---|---|---|---|
| (1) | Fresh frozen plasma | 0.5 | 8000 | 4000 | 8.0 | 240 | 1200 | 800 | 480 | Blood bank |
| (2) | Cryoprecipitate | 10 [3/] | 400 | 4000 | 4.0 | 20 | 40 | 40 | 400 | Blood bank |
| (3) | Factorate | 10 | 400 | 4000 | 0.8 | 14 | 96 | 80 | 480 | Armour pharmaceutical |
| (4) | AHF | 10 | 400 | 4000 | — [4/] | 20 | 80 | 48 | 480 | Abbott Laboratory |
| (5) | Hemofil | 25 | 160 | 4000 | 1.0 | 5.6 | 25 | 20 | 528 | Hyland |
| (6) | AHF [5/] | 10 | 400 | 4000 | | 6.0 | | | | Shanbrom |
| (7) | AHF [6/] | 10 | 400 | 4000 | | 2.0 | | | | Shanbrom |

[1/] This table, except for the "Shanbrom" entries are from "Recent Advances in Hemophilia" Ann. N.Y. Acad. Sciences 240:165-171, 1975, Robert T. Breckenridge. The Shanbrom entries result from the invention described herein.
[2/] These Figures are based upon the experience of the Hemophilia Center of Rochester and Monroe County and are expressed as totals necessary to treat a 70-kg patient to one unit per ml. They assume a recovery of 80% in vivo.
[3/] Variable, but usually between 7-12 μ/ml.
[4/] Unable to measure fibrinogen due to precipitation at 37° C.
[5/] Described in Application Serial No. 586,958, Filed June 16, 1975.
[6/] Polyol precipitation in the cold described herein in detail and in S.N. 586,958, Filed June 16, 1975.

The need for a high yield, high purity freeze-dried AHF concentrate has received international recognition and concern (11, 12) and it is generally agreed that commercial concentrates usually yield less than 20% of the theoretical AHF present in plasma, while highly purified products are even lower (11-Pg. 156, 208; 5, 8).

EXAMPLE METHOD I

Frozen plasma, e.g., 100 to 3000 liters, is thawed at from about −5° C to about +2° C and collected in an appropriate tank or vessel. Greater volumes may be handled but operations become difficult. The cold insoluble fraction (cryoprecipitate) is collected, preferably in continuous flow centrifuges (Sharpless or similar centrifuges), at less than 3° C. Other collection methods may be used but are less efficient. The cryoprecipitate is weighed, cut into small pieces or mixed in a Waring-type blender for a few seconds to produce a slurry or emulsion. The cryo pieces or slurry are then dissolved in from 2 to 4 volumes of buffer consisting of 0.02 molar trisodium citrate and 0.1 molar glycine adjusted with citric acid to pH 6.9 at temperatures of 20°-30° C. After dissolution is complete, fibrinogen is selectively precipitated by the addition of 4% polyethylene glycol 4000 or Pluronic F-68 at pH 6.0 to 6.5 and temperature of about 25° C. The precipitate is removed by Sharpless-type continuous centrifugation and the supernatant fluid is adjusted to pH 6.8-7.2. An additional 2% PEG or Pluronic F-68 is added and the suspension is cooled to 0°-5° C until visible precipitation occurs.

cartridge equivalents) having typically 1.2, 0.65, 0.45 and 0.3 micron diameter pores. The resulting sterile solution, containing from about 20-40% of the Factor VIII in the original plasma starting material is lyophilized in the normal manner for storage.

Variation of manufacturing technique, particularly employing refrozen cryoprecipitate or variants of Cohn Fraction I may be employed, although in such situations the yield of Factor VIII will be lessened and is dependent on its concentration in the starting material. Original dissolution or extraction of AHF may be carried out in distilled water or low ionic strength buffers such as Tris buffer. Cooling time may also be varied, increased or performed repetitively without departing from the invention. Likewise, extraction time can be increased to up to 24 hours within the procedure described. In addition, the procedure may be interrupted at any step and continued on a subsequent day. All such variations may cause some reduction in the overall yield of AHF from the starting plasma.

EXAMPLE METHOD II

Pyrogenic lots of Factor VIII concentrate of intermediate purity made by any other method, such as low ionic strength buffer extraction, glycine precipitation, PEG precipitation, etc., may be reworked according to the schema outlined in Example Method I. The lyophilized vials are reconstituted in a volume of pyrogen-free water sufficient to produce a protein content of 1-3 Gm %. The vials are then pooled and reprocessed according to the steps outlined in Example Method I.

Alternatively, if the pyrogen levels are only modestly elevated and if the product is already of high purity, a single step of precipitation may be all that is required. The vials are reconstituted as described above and 6% PEG is added at a pH of 6.8-7.2 at a temperature of 0°-5° C. The precipitation formed is then treated as before and the supernatant fluid containing solubilized pyrogenic material is discarded.

EXAMPLE METHOD III

The procedure described in Example Method I is carried out. However, before the final filtration steps are done the product is placed in a cold room (0.5° to 5°) and allowed to stand for 12-24 hours. The white flocculant material which forms after this period of standing is removed by decantation, centrifugation or pre-filtration. The final product is sterile filtered as previously described and submitted to the same freeze-drying procedures. This product is even more highly purified than the previous products and thus more easily filtered. There is no loss of Factor VIII from this additional step.

The resultant products can be stored at +5° C for a long period of time, one or two years, and reconstituted in distilled water or physiologic silane. Because of its very high purity and exceedingly low fibrinogen content, the lyophilized product goes into solution very quickly (1-2 minutes). Since the entire processing time is very short compared to other methods of manufacture from the time that the bags of plasma are opened, bacterial growth is limited. The fact that the initial dissolution is carried out in only small amounts of buffer decreases the amount of gamma globulins which go into solution and optimum precipitation of excessive fibrinogen occurs by using a polyol concentration of 4%. In addition, the heavy flocculant precipitate of fibrinogen probably entraps pyrogenic material present and reduces amounts of hepatitis-associated antigen (HAA or hepatitis virus). By employing only 6% polyol in the cold precipitation step, undesirable proteins, particularly isohemagglutinins which may have dissolved even in the lessened volumes of buffer, are not precipitated with the AHF and are discarded with the supernate. This results in a product purified 200 to 400 times, over plasma, and very low in fibrinogen and isohemagglutinins. Factor VIII concentrates manufactured with larger volumes of extracting buffer, e.g., 10 volumes (2) do not exhibit this degree of efficiency in purification of yield of AHF (1, 2, 3, 4, 8), probably because optimum ratio of protein and polymer for coprecipitation have not been achieved. If desired, this product can be further purified and concentrated by known procedures or new procedures. One great advantage of this invention is that large-scale production of very pure AHF can be produced in one-half to two-thirds the time required with other procedures.

The examples given before are the optimum procedures presently known for carrying out the invention. It will be apparent, however, that the invention may be practiced through the application of conventional processing techniques and materials to principle of the invention. For example, while it is generally not economically practicable to start with less than about 100 liters of plasma, or cryoprecipitate from this amount of plasma, there if obviously no criticality to either the upper or lower volume values given in the example and variations by fifty percent or so in these values would not affect the invention. The procedures in the optimum example are carried out using well-known and readily available equipment, such as the Sharpless centrifuge, the Waring blender, etc., but all will recognize that these steps per se, in isolation from the inventive principle, and the equipment involved are not critical and great variation can be made within the invention within the discretion of the operator, depending upon available manpower, equipment, etc. Once the supernatant liquid, containing the Factor VIII in high recovery, is obtained, it is treated in the conventional manner for storage and reconstitution; e.g., it is clarified and sterilized, through standard micropore filtration, lyophilized to concentrate the Factor VIII into a small, easily storable volume, and reconstituted using conventional liquids, e.g., pyrogen-free water or physiologic saline.

The invention is limited by the claims set forth hereinafter, and not by the specific details of the exemplary procedure set forth in the specification as the best mode. The product which results has characteristics which are unique, beneficial to the patient, and distinctive from all other Factor VIII concentrates presently manufactured:

1. Highest purification and therefore highest "specific activity."
2. Highest solubility, rate and ultimate solubility, making it ideal for emergency treatment.
3. Lowest protein which decreases undesirable side reactions.
4. Lowest immunoglobulins which decreases allergic reactions.
5. Negligible isohemagglutinins which eliminates hemolytic reactions.
6. Lowest clottable fibrinogen which decreases complications of hyperfibrinogenemia.
7. Since not filter needle is required the hazard of foreign particulate matter is eliminated.
8. Elimination of pyrogens during the process conserves utilizable Factor VIII.

These and other advantages accrue from the process described herein, illustrated by non-limiting examples, and defined in scope in the claims. In summary, the inventive process for preparing Factor VIII concentrate is the discovery that by holding a buffer solution containing Factor VIII and about 6% polyol at a temperature of from about 0° to about 5° precipitation of the Factor VIII occurs, thus producing a very high purity Factor VIII product which is substantially free of contaminating foreign protein. Polyol, as referred to herein, includes polyethylene glycol and the Pluronic series polyols described hereinbefore and discussed in greater detail in the parent application Ser. No. 586,948, filed June 16, 1975, the disclosure of which is included herein by reference.

The invention is also an improvement in a process for preparing Factor VIII concentrate comprising precipitating fibrinogen selectively from a solution of plasma or plasma cryoprecipitate in buffer by the addition of about 4% by volume of polyol to said solution, concentrating the Factor VIII in the solution by increasing the polyol concentration to about 6% and holding the 6% polyol containing solution at from about 0° to about 5° C until precipitation occurs and then redissolving the precipitated Factor VIII in buffer solution to yield a solution containing very high purity Factor VIII which is substantially free of contaminating foreign protein.

In the preferred mode, cryoprecipitate is dissolved in 2 to 4 times the volume thereof, and preferably 3 volumes, thereof, of buffer, citrate buffer being greatly preferred. Dissolution in this volume of buffer plus the addition of the polyol results in extremely and unpredictably efficient precipitation of very high purity Factor VIII with little loss in any preliminary precipitation of fibrinogen. The process is further enhanced by redissolving the precipitated Factor VIII in citrate buffer and holding the resulting solution at a temperature of from about 0.5° to about 5° C for a time period from about 12 to about 24 hours and thereafter separating particulate matter formed from said solution to thereby further free Factor VIII from fibrinogen, fibrinogen fragments and complexes of the same.

The result never before accomplished effectively may be effected by applying the inventive process as a method of re-working or re-manufacturing Factor VIII concentrate or removing pyrogens from Factor VIII concentrates prepared by any method. In this process, Factor VIII in buffer solution, preferably citrate buffer, is treated by the addition of about 6% polyol to said solution and holding the resulting polyol containing solution at a temperature of from about 0° to about 5° C to thereby precipitate Factor VIII, leaving in solution the pyrogenic material.

In a preferred modification of the foregoing process, polyol is added to such buffer solutions of Factor VIII in two steps, first adding about 4% polyol followed by separation of precipitate from the solution and the addition of 2% polyol and maintaining the solution at from about 0° to 5° until precipitation of Factor VIII occurs.

This process is also enhanced by redissolving the precipitated Factor VIII in citrate buffer and holding the resulting solution at a temperature of from about 0.5° to about 5° C for a time period from about 12 to about 24 hours and thereafter separating particulate matter formed from said solution to thereby further free Factor VIII from fibrinogen, fibrinogen fragments and complexes of the same.

REFERENCES CITED IN THE SPECIFICATION

1. Wickerhauser, M.: Large-scale fractionation of Factor VIII — Concentrate from cryoethanol precipitate.
2. Shanbrom, E. & Fekete, L.: Production of stable high-potency human AHF using polyethylene glycol and glycine to fractionate a cryoprecipitate of AHF concentrate. U.S. Pat. No. 3,631,018, Dec. 18, 1971.
3. Sgouris, J. T. and Wickerhauser, M.: Use of frozen cryoprecipitate for the preparation of clinical Factor VIII concentrate. Transfusion 13:399, 1973.
4. Newman, Johnson, A. J., Karpatkin, M. H. and Puszkin, S.: Methods for the production of clinically effective intermediate and high-purity Factor VIII concentrates. Brit. J. Haemat, 1971, 21I.
5. Fekete, L. F. and Holst, S. L.: Stabilization of AHF using Heparin. U.S. Pat. No. 3,803,115, Apr. 9, 1974.
6. Johnson, A. J., Newman, J., and Karpatkin, M. H.: Antihemophilic factor prepared from blood plasma using polyethylene glycol. U.S. Pat. No. 3,652,530, Mar. 28, 1972.
7. Shanbrom, E.: A simple method for the production of high yield, high purity Factor VIII, Application Ser. No. 586,948, Filed June 16, 1975.
8. Vermeer, C., Soute, B. A. M., and Brummelhuis, H. G. J.: Improvement of the preparation of Factor VIII Concentrates. Proc. of Int. Soc. Haemostasis and Thrombosis, Paris, July, 1975 (Abstract).
9. Seeler, R. A., Telischi, M., Langehennig, P. L. and Ashenhurst, J. B.: Anti-A and Anti-B titers in coagulation concentrates. Abst. of Int. Soc. of Blood Transf., Helsinki, 1975.
10. Couper. I. A., McAdam, J. H., MacKenzie, M. S. and Davidson, J. F.: Contamination of Factor VIII concentrates with metal particles. Lancet, Dec. 21, 1974. pg. 1515.
11. Recent Advances in Hemophilia. Ann. N.Y. Acad. Sci. 240, 1975.
12. Pool, J. G.: Recent chapters in the Factor VIII saga: perils of a protein. West J. of Med., 122:406, 1975.

What is claimed is:

1. In a process for preparing Factor VIII concentrate, the improvement comprising the step of holding a buffer solution containing Factor VIII and about 6% polyol at a temperature of from about 0° to about 5° C until precipitation occurs.

2. In the process for preparing Factor VIII concentrate, the improvement comprising the step of precipitating fibrinogen selectively from a solution of plasma or plasma cryoprecipitate in buffer by the addition of about 4% by volume of polyol to said solution, concentrating the Factor VIII in the solution by increasing the polyol concentration to about 6% and holding the 6% polyol containing solution at from about 0° to about 5° until precipitation occurs and then redissolving the precipitated Factor VIII in buffer solution to yield a solution containing very high purity Factor VIII which is substantially free of contaminating foreign protein.

3. The process of claim 2 wherein the source of Factor VIII is cryoprecipitate dissolved in from about 2 to about 4 times the volume thereof in citrate buffer.

4. The process of claim 3 wherein the volume ratio of the cryoprecipitate to buffer is about 1 to 3.

5. In a process for removing pyrogens from a buffer solution of Factor VIII the improvement comprising the addition of about 6% polyol to said solution and holding the resulting polyol containing solution at a temperature of from about 0° to about 5° C to thereby precipitate Factor VIII, leaving in solution the pyrogenic material.

6. In the process of claim 5 the addition of polyol to buffer solutions of Factor VIII in two steps, first adding about 4% polyol followed by separation of precipitate from the solution and the addition of 2% polyol and maintaining the solution at from about 0° to 5° until precipitation of Factor VIII occurs.

7. The process of claim 5 wherein the solution contains about 1 to 3 gram percent protein.

8. In the concentration of Factor VIII the improvement comprising holding a solution of about 1 part of Factor VIII containing blook fraction obtained from plasma cryoprecipitation in about 3 parts of citrate buffer containing about 6% polyol at a temperature of from about 0° to 5° to thereby cause precipitation of Factor VIII from said solution and redissolving said Factor VIII in buffer to give a very high purity Factor VIII containing solution.

* * * * *